United States Patent [19]

Brazdil et al.

[11] Patent Number: 4,921,828

[45] Date of Patent: May 1, 1990

[54] ANTIMONY PROMOTED BISMUTH CERIUM MOLYBDATE CATALYSTS

[75] Inventors: James F. Brazdil, Mayfield Village; Linda C. Glaeser, Middleburg Hts.; Robert K. Grasselli, Chagrin Falls, all of Ohio

[73] Assignee: The Standard Oil Company, Cleveland, Ohio

[21] Appl. No.: 212,048

[22] Filed: Jun. 24, 1988

Related U.S. Application Data

[63] Continuation of Ser. No. 781,547, Sep. 10, 1985, abandoned, which is a continuation of Ser. No. 671,267, Nov. 13, 1984, abandoned, which is a continuation-in-part of Ser. No. 391,785, Jun. 24, 1982, abandoned.

[51] Int. Cl.$^5$ .................. B01J 23/10; B01J 23/18; B01J 23/30

[52] U.S. Cl. .................. 502/205; 502/212; 502/215; 502/304

[58] Field of Search ............... 502/205, 212, 215, 304

[56] References Cited

U.S. PATENT DOCUMENTS

| | | | |
|---|---|---|---|
| 3,262,962 | 7/1966 | McDaniel et al. | 260/465.3 |
| 3,541,129 | 11/1970 | Yamada et al. | 260/465.3 |
| 4,118,419 | 10/1978 | Ishii et al. | 502/212 X |
| 4,414,133 | 11/1983 | Otake et al. | 502/304 X |

FOREIGN PATENT DOCUMENTS 0032618  7/1981  European Pat. Off. ............ 502/304

Primary Examiner—W. J. Shine
Attorney, Agent, or Firm—Larry W. Evans; David J. Untener; Michael F. Esposito

[57] ABSTRACT

Antimony-promoted bismuth cerium molybdate catalysts are promoted with additional elements.

2 Claims, No Drawings

ANTIMONY PROMOTED BISMUTH CERIUM MOLYBDATE CATALYSTS

This is a continuation of application Ser. No. 781,547 filed Sept. 10, 1985, now abandoned, which is a continuation of application Ser. No. 671,267 filed on Nov. 13, 1984, now abandoned, which is a continuation-in-part of application Ser. No. 391,785 filed on June 24, 1982, now abandoned.

BACKGROUND OF THE INVENTION

Commonly assigned application Ser. No. 258,708, filed Apr. 29, 1981, describes catalyst systems for ammoxidizing propylene to produce acrylonitrile and for carrying out other oxidation-type reactions such as the oxidation of unsaturated olefins to produce the corresponding aldehydes and acids and the oxydehydrogenation of various olefins to produce diolefins.

The catalyst systems described in that patent application comprise bismuth cerium molybdate oxide complexes promoted with one or more specific promoting elements. One such promoter is antimony.

Further research has shown that the antimony-promoted bismuth cerium molybdates show excellent catalytic properties when initially used in the ammoxidation of propylene and isobutylene. Unfortunately, it has been found that the ability of these catalysts to produce acrylonitrile and methacrylonitrile drops off significantly with time.

Accordingly, it is an object of the present invention to provide an improvement in the antimony-promoted bismuth cerium molybdates of Ser. No. 258,708 whereby the tendency of the catalyst to lose effectiveness over time is significantly reduced.

In addition it is further object of the present invention to provide new catalysts which are also useful in other oxidation-type reactions such as the oxidation of acrolein and methacrolein to produce the corresponding unsaturated aldehydes and acids and the oxydehydrogenation of various olefins such as isoamylenes to produce the corresponding diolefins such as isoprene.

SUMMARY OF THE INVENTION

These and other objects are accomplished by the present invention which is based on the discovery that the incorporation of certain elements into the antimony-promoted bismuth cerium molybdate redox catalysts of Ser. No. 258,708 remarkably reduces the tendency of the catalysts to lose effectiveness when used in various oxidation-type reactions such as the ammoxidation of propylene to produce acrylonitrile.

Thus, the present invention provides an improvement in known antimony-promoted bismuth cerium molybdate redox catalysts wherein a promoting amount of Fe, Mn, Pb, Co, Ni, Cu, Sn, U, Ge, As, P, B, Se, a Group IIA element or mixture thereof is incorporated into the catalyst.

In addition, the present invention provides an improvement in the known process for ammoxidizing propylene to produce acrylonitrile by contacting propylene, ammonia and molecular oxygen with an antimony-promoted bismuth cerium molybdate oxidation catalyst at an elevated temperature, the improvement wherein at least one of the above-noted promoter elements are incorporated into the catalyst.

DETAILED DESCRIPTION

Catalysts

Bismuth cerium molybdate redox catalysts are known. See, for example, the McDaniel and Young U.S. Pat. No. 3,173,957, 3,262,962 and 3,316,182, the disclosures of which are incorporated herein by reference. Incorporation of antimony into such catalysts to improve catalytic performance is shown in Ser. No. 258,708, the disclosure of which is incorporated herein by reference. In accordance with the invention it has been found that the incorporation of certain additional elements into such catalysts will reduce the tendency of these materials to lose catalytic effectiveness with time. By this it is meant that the catalyst without the effective promoters tend to get lower conversion to the desired product after use over time, and that the promoter decreased this tendency. Examples of this are shown in Table 1. Furthermore, catalysts of the invention produce by-product effluents with very low chemical oxidation demand (COD) and are thus environmentally superior to many known redox catalysts such as the iron bismuth molybdates.

The elements found to be effective promoters in accordance with the invention are (1) Fe, Mn, Pb, Co, Ni, Cu, Sn and U, preferably Fe, Co and/or Mn and (2) Ge, As, P, B, Se and a Group IIA element, preferably Mg. These elements can be incorporated into the bismuth cerium molybdate base systems alone or in mixtures.

The catalysts of the invention correspond to the following general formula:

$$A_a D_b Sb_c Bi_d Ce_e W_f Mo_g O_x$$

wherein
- A is Fe, Mn, Pb, Co, Ni, Cu, Sn, U or mixtures thereof, preferably Fe, Mn and Co or mixtures thereof,
- D is Ge, As, P, B, Se, a Group IIA element or mixture thereof, preferably Mg and wherein
- a is 0 to 24, preferably 0 to 6, more preferably 0 to 4;
- b is 0 to 24, preferably 0 to 6, more preferably 0 to 4;
- a+b is greater than 0, preferably at least 0.1, more preferably 0.1 to 4;
- c is greater than 0 to 16, preferably 0.1 to 6, more preferably 0.1 to 3;
- d is 0.01 to 24, preferably 0.5 to 8, more preferably 1 to 5;
- e is 0.01 to 24, preferably 0.5 to 8, more preferably 1 to 5;
- d+e is preferably 5 to 10;
- a+b+d+e is preferably 6 to 10;
- d/e is preferably ¼ to 4/1, more preferably ½ to 2/1;
- f is 0 to 8, preferably 0 to 4;
- g is 8 to 16, preferably 10 to 12; and
- f+g is 8 to 16, preferably 12.

The catalysts of the invention can also include promoter elements disclosed in Ser. No. 258,708 other than antimony. In this case, the catalyst of the invention correspond to the formula

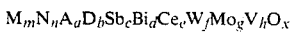

$$M_m N_n A_a D_b Sb_c Bi_d Ce_e W_f Mo_g V_h O_x$$

wherein
- M is alkali metal, Tl, Sm, Ag, Cu or mixtures thereof, preferably K, Rb and/or Cs;

N is Ti, Zr, Th, Te, Cr or a Rare Earth element other than Sm and Ce; and
wherein
m is 0 to 6, preferably 0 to 2;
n is 0 to 24, preferably 0 to 8;
h is 0 to 2; and
wherein
A, D, a, b, c, d, e, f, g, and x are as described above. Such catalysts preferably contain vanadium and/or an alkali metal, most preferably cesium.

In another embodiment of the present invention, the catalyst corresponds to the formula:

$$A_aD_bSb_cBi_dCe_eW_fMo_gV_hO_x$$

wherein
A is Co, Fe, Mn, Pb or mixture thereof,
D is Ge, As, B, Se, a Group IIA element or mixtures thereof; and
a is about 0.5 to about 1,
b is 0 to 24,
c is about 1,
d is about 4,
e is about 4,
f is about 2,
g is about 10,
h is 0 to about 0.1; and
x is a number sufficient to satisfy the valence requirements of the other elements present.

The above formulas in general describe the catalysts produced by the invention. However, as will be appreciated by those skilled in the art, such formula descriptions do not connote that every material following therein will exhibit superior effectiveness as a catalyst. Rather such descriptions connote only that catalysts of the invention will have compositions corresponding to the above formulas. Those skilled in the art readily understand that a catalyst, in order to exhibit good catalytic properties, must have an appropriate balance of ingredients and that too much of any one element can drastically reduce its effectiveness or even inactivate the catalyst. The same considerations apply to this invention. The base catalyst systems must be compounded so as to have an appropriate balance of ingredients for catalyzing the specific reaction of interest. In addition, the exact amount of A, D, M or N promoter element to be incorporated therein, either by adding the promoter to the existing system ot substituting some of the Bi and/or Ce content of the base system with promoter, must also be appropriately selected. In accordance with the invention, the incorporation of the above-described A and D elements into known bismuth cerium molybdate catalysts will exhibit a promoting effect on the catalysts in various oxidation-type reactions. Those skilled in the art can easily determine how much of a particular A and/or D element should be incorporated into a particular antimony-promoted bismuth cerium molybdate base system to promote a particular oxidation-type reaction by simply routine experimentation, especially in view of the following working examples.

The catalysts of the invention can be used either in unsupported form or supported on suitable carriers such as $SiO_2$, $Al_2O_3$ and the like. The catalysts can also be coated on these supports by special techniques known in the art.

These catalysts can be prepared by conventional techniques such as disclosed in Grasselli, et al. U.S. Pat. No. 3,642,930. These catalysts are most easily prepared by slurry techniques wherein an aqueous slurry containing all of the elements in the objective catalyst is produced, the water removed from the aqueous slurry to form a precatalyst precipitate or powder and the precatalyst then heated in the presence of an oxygen-containing gas such as air at elevated temperature to calcine the precatalyst thereby forming the catalyst. Liquids other than water, such as $C_1$ to $C_8$ alcohols can also be used to form the precatalyst slurry.

AMMOXIDATION

The catalysts of the invention find significant use in the ammoxidation of propylene to produce acrylonitrile. This reaction is well known and described, for example, in the above-noted Grasselli, et al. patents. In general, the ammoxidation reaction is accomplished by contacting the reactant, oxygen and ammonia with a particular catalyst in the vapor phase. The inventive reaction is carried out in the same manner and under the conditions generally set forth in these patents.

In a preferred aspect, the inventive process comprises contacting a mixture comprising propylene, ammonia and oxygen with the catalyst of this invention at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hydrocarbons to the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e. in the range of 0.15:1 to 0.75:1. Above the upper limit of this range, the amount of aldehydes produced rapidly decreases. Within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are within the scope of the present invention and are preferred in the fluid-bed operation.

In general, the molar of added water to olefin, when water is added, is in the neighborhood of 0.1:1 or higher. Ratios on the order of 1:1 to 6:1 are particularly desirable, but higher ratios may be employed, i.e. up to about 10:1.

The reaction is carried out at an elevated temperature such as 200° to 600° C., preferably 400° to 550° C., more preferably 420° to 500° C. The reaction should be carried out at about atmospheric or slightly above atmospheric (2 to 3 atmospheres) pressure. In general, high pressure, i.e. above 15 atmospheres, are not suitable since higher pressures tend to favor the formation of undesirable by-products.

The apparent contact time is not critical, and contact times in the range of from 0.1–40 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a vapor. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

In addition to propylene, other hydrocarbons and oxygenated hydrocarbons can be ammoxidized with the catalyst of the invention. For example, alcohols such as isopropanol, n-propanol, t-butyl alcohol, and aldehydes such as acrolein and methacrolein can be readily converted to nitriles in accordance with the present invention. In addition to propylene, other preferred starting materials are aldehydes and alcohols containing three or four carbon atoms. The general ammoxidation process for converting olefins, alcohols and aldehydes to nitrile is well known and described for example in U.S. Pat. No. 3,456,138, the disclosure of which is incorporated herein by reference.

OXIDATION

The catalysts of this invention can also be employed in the catalyst oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain). Instead of olefins, alcohols such as isopropanol, n-propanol or tert-butanol can be used as reactants.

The olefins or alcohols may be in admixture with paraffinic hydrocarbons, such as ethane, propane, butane and pentance. For example, a propylene-propane, butane and pentane. For example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° to 600° C. may be advantageously employed. However, the process may be conducted at other pressures, e.g. above 5 atmospheres are employed, somewhat lower temperatures are possible. In the case where this process is employed to convert propylene to acrolein, a temperature range of 200° to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired by-products and waste is diminished.

The apparent contact time employed in the process is critical and it may be selected from a broad operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:0.25 to 1:10 will give very satisfactory results while a ratio of 1:0.5 to 106 has been found the optimum when converting propylene to acrolein.

Inert diluents such as nitrogen and carbon dioxide may be present in the reaction mixture.

OXYDEHYDROGENATION

In accordance with the present invention, the catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquanternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methylbutene-1, 2-methylbutene-2, 3-methylbutene-1, 2-methylpentene-1, 3-methylpentene-2, 4-methylpentene-2, heptene-1, 3,4-dimethyl-pentene-1, octene-1, cyclopentene, cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to insure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 200° to 800° C. Optimum yields are obtainable at temperatures within the range from about 300° to 600° C.

The preferred reaction pressure is approximately atmospheric, within the range of from about 0.1 to about 5 atmospheres.

Only a brief contact time with the catalyst is required for effective oxydehydrogenation. The apparent contact time with the catalyst can vary from about 0.1 up to about 50 seconds but higher contact times can be used if desired. At the short contact times, comparatively small reactors and small amounts of catalyst can be used effectively.

PROCESS CONDITIONS

In carrying out the foregoing processes, any apparatus of the type suitable for carrying out the oxidation reactions in the vapor phase may be employed. The processes may be conducted either continuously or intermittently. The catalyst may be fixed-bed employing a particulate or pelleted catalyst or, in the alternative, a fluid-bed catalyst may be employed which is normally micro-spheroidal.

WORKING EXAMPLES

In order to more thoroughly describe the present invention, the following working examples are presented. In these examples, the following definitions apply:

$$\text{"Yield" means } \frac{\text{moles product formed}}{\text{moles reactant fed}} \times 100$$

$$\text{"Selectivity" means } \frac{\text{moles product formed}}{\text{moles reactant reacted}} \times 100$$

In each of the examples and comparative examples, a catalyst having the composition set forth in the following tables was prepared in accordance with a standard laboratory preparation.

EXAMPLES 1 TO 4 AND COMPARATIVE EXAMPLES A TO E

Four catalysts of the invention and five comparative catalysts were tested in the known ammoxidation reaction for producing acrylonitrile from propylene. In each example and comparative example each catalyst was supported on 50% silica 2.5 cc of the catalyst together with 3.5 cc of glass wool were charged into a 6 cc fixed-bed microreactor and contacted with a feed comprising 1 propylene/1.2 $NH_3$/10.5 air/4 $H_2O$ at elevated temperature for a contact time of 3 seconds. The gross reaction product recovered from each experiment was the analyzed.

The composition of the catalysts, the reaction temperatures and the results obtained are set forth in the following Table 1.

TABLE 1

Temp. - 460° C., 3.0 sec contact time.
2.5 cc of catalyst, 1 $C_3^=$/1.2 $NH_3$/10.5 air/ 4 $H_2O$

| Ex. No. | Composition | Time On Stream(hrs) | Yields Acrylonitrile | HCN | Acrylonitrile Selectivity |
|---|---|---|---|---|---|
| A | $Cs_{0.05}Bi_4Ce_4Mo_{10}W_2O_x$ | 1 | 77.0 | 3.3 | 78.3 |
| B | $Cs_{0.05}Bi_4Ce_4Sb_{0.5}Mo_{10}W_2O_x$ | 1 | 80.0 | 2.3 | 81.7 |
| C | $Cs_{0.05}Bi_4Ce_4Sb_{0.5}Mo_{10}W_2O_x$ | 31 | 74.8 | 3.1 | 82.9 |
| D | $Bi_4Ce_4Sb_1Mo_{10}W_2O_x$ | 1 | 80.9 | 2.2 | 82.0 |
| E | $Bi_4Ce_4Sb_1Mo_{10}W_2O_x$ | 26 | 74.3 | 2.7 | 83.0 |
| 1 | $Bi_4Ce_4Co_1Sb_1Mo_{10}W_2O_x$ | 41 | 79.3 | 4.0 | 80.0 |
| 2 | $Bi_4Ce_4Fe_{0.5}Sb_1Mo_{10}W_2O_x$ | 67 | 78.8 | 4.8 | 79.7 |
| 3 | $Bi_4Ce_4Mg_{0.5}V_{0.1}Sb_1Mo_{10}W_2O_x$ | 18 | 82.1 | 3.3 | 83.7 |
| 4 | $Bi_4Ce_4Mg_{0.5}V_{0.1}Sb_1Mo_{10}W_2O_x$ | 42 | 79.3 | 3.2 | 82.8 |

The above data, and particularly a comparison of Comparative Examples B and D with C and E, respectively, shows that although antimony-promoted bismuth cerium molybdates are capable of promoting the formation of acrylonitrile with high yields initially, they undergo a significant loss in catalytic effectiveness by the time the catalysts have been on stream for about thirty hours or so. In contrast, Examples 1 to 4 show that inclusion in the catalyst of a promoter element in accordance with the invention significantly reduces this loss in effectiveness, the catalysts after thirty or more hours of operation are still producing acrylonitrile in excellent yields.

Although only a few embodiments of the present invention have been described above, it should be appreciated that many modifications can be made without departing from the spirit and scope of the invention. All such modifications are intended to be included within the scope of the present invention, which is to be limited only by the following claims:

We claim:

1. An antimony promoted bismuth cerium molybdate oxide catalyst free of Phosphorus having the formula:

$$A_a D_b Sb_c Bi_d Ce_e W_f Mo_g O_x$$

wherein

A is Fe, Mn, Pb, Co, Ni, Cu, Sn, U, or mixtures thereof,

D is Ge, As, B, Se, a Group IIA element or mixtures thereof, and wherein a is 0 to about 1,
b is 0 to 24,
a+b is greater than 0,
c is greater than 0 to 16,
d is 0.01 to 24,
e is 0.01 to 24,
d+e is 5 to 10,
a+b+c+d is 6 to 10,
d/e is 1/4 to 4/1,
f is 0 to 8,
g is 8 to 16,
f+g is 8 to 16, and
x is a number of oxygen atoms required to satisfy the valence requirements of the other elements.

2. The antimony promoted bismuth cerium molybdate oxide catalyst of claim 1 wherein a is about 0.5 to about 1.

UNITED STATES PATENT AND TRADEMARK OFFICE
CERTIFICATE OF CORRECTION

PATENT NO. : 4,921,828

DATED : May 1, 1990

INVENTOR(S) : Brazdil et al.

It is certified that error appears in the above-identified patent and that said Letters Patent is hereby corrected as shown below:

Column 3, line 14, "$Bl_d$" should read --$Bi_d$--. Column 4, line 66, should include --ratio-- following "molar". Column 6, line 48, "106" should read -- 1:6 --.

Signed and Sealed this

Twenty-sixth Day of November, 1991

Attest:

HARRY F. MANBECK, JR.

*Attesting Officer*    *Commissioner of Patents and Trademarks*